United States Patent [19]

Klein et al.

[11] Patent Number: 5,288,721
[45] Date of Patent: Feb. 22, 1994

[54] SUBSTITUTED EPOXYALKYL XANTHINES

[75] Inventors: J. Peter Klein, Vashon; David Porubek, Edmonds; Glenn C. Rice, Seattle; Paul Woodson, Bothell, all of Wash.

[73] Assignee: Cell Therapeutics, Inc., Seattle, Wash.

[21] Appl. No.: 949,330

[22] Filed: Sep. 22, 1992

[51] Int. Cl.⁵ .................. A61K 31/52; C07D 473/04
[52] U.S. Cl. ................................. 514/263; 544/267
[58] Field of Search ..................... 544/267; 514/263

[56] References Cited

U.S. PATENT DOCUMENTS

| | | | |
|---|---|---|---|
| 3,373,433 | 6/1973 | Mohler et al. | 260/256 |
| 3,422,107 | 1/1969 | Mohler et al. | 260/256 |
| 4,031,218 | 6/1977 | El-Antably | 544/267 |
| 4,515,795 | 5/1985 | Hinze et al. | 514/263 |
| 4,576,947 | 3/1986 | Hinze et al. | 544/267 |
| 4,636,507 | 1/1987 | Kreutzer et al. | 514/263 |
| 4,833,146 | 5/1989 | Gebert et al. | 544/267 |
| 4,960,773 | 10/1990 | Korbonits et al. | 544/267 |
| 4,965,271 | 10/1990 | Mandell et al. | 514/263 |
| 5,039,666 | 8/1991 | Novick, Jr. | 514/39 |
| 5,096,906 | 3/1992 | Mandell et al. | 514/263 |
| 5,175,291 | 12/1992 | Kufner-Muhl | 544/267 |

OTHER PUBLICATIONS

Fisher et al., Arzneim-Forsch/Drug Res., 34(1) No. 6; p 666; 1984.
Davis et al., *Applied Environment. Microbiol.* (1984) 48:327–331.

*Primary Examiner*—John M. Ford
*Assistant Examiner*—P. K. Sripada
*Attorney, Agent, or Firm*—Jeffrey B. Oster; Kate H. Murashige

[57] ABSTRACT

Compounds of the formula

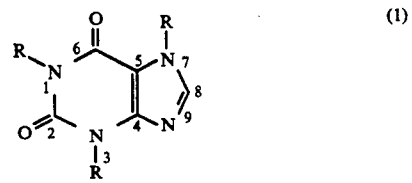

(1)

including the resolved enantiomers and/or diastereomers and mixtures thereof wherein each of one or two R is independently

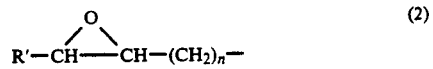

(2)

wherein n is 1-16 and R' is H or alkyl(1-4C); and wherein each remaining R is independently H, alkyl(1-6C), alkenyl(1-6C) or benzyl; an wherein said alkyl or alkenyl may be substituted by a hydroxyl, halo, or dimethylamino group, and/or interrupted by an oxygen atom, are useful in modulating the effects of internal and external stimuli on cells by reversing the effects of these stimuli on the short-term secondary messenger pathways. In particular, the compounds lower elevated levels of unsaturated, non-arachidonate phosphatidic acid (PA) and diacylglycerol (DAG) derived from said PA within seconds of the primary stimulus and their contact with said cells. The modulatory effect depends on the nature of the target cell and the stimulus applied.

12 Claims, 5 Drawing Sheets

SUBSTITUTED EPOXYALKYL XANTHINES

TECHNICAL FIELD

The invention relates to modulation of cellular responses to external stimuli by control of the short-term secondary responses to primary cell-affecting agents. More specifically, the invention concerns the use of xanthines with at least one epoxide-containing substituent on a ring nitrogen to control elevations in the level of specific sn-2 unsaturated phosphatidic acid and the corresponding phosphatidic acid-derived diacylglycerol which occur in response to these stimuli.

BACKGROUND ART

The general outlines of the mechanisms by which external stimuli effect the behavior of target cells have been described in general Molecular Biology textbooks over the last 10-20 years. For at least some of these stimuli, a primary interaction of the stimulating agent at a cell surface receptor is translated into an effect on various secondary signaling pathways internal to the cell, which secondary signaling pathways in turn produce the observed effect on cellular behavior. Most of these secondary pathways involve the synthesis and hydrolysis of phosphorylated acyl glycerol derivatives such as phosphatidic acid, phosphatidyl inositol, phosphatidyl ethanolamine, lysophosphatidic acid, and so forth. The synthesis and release of the components of these compounds can result in cellular proliferation, suppression of proliferation, differentiation, activation, and so forth, depending upon the nature of the target cell and the stimulus applied.

The pathways regulating the synthesis and degradation of phosphorylated derivatives of acyl glycerols are complex and interlocking. Certain effects of external stimuli are seen immediately—i.e., within a few seconds or a minute; others are seen 30-60 minutes after the external stimulus has bound to the surface receptor of the cell. It is believed that the short-term effects on these second messengers are associated with the stimulus itself and are not appreciably interconnected with those aspects of the phosphorylated acyl glycerol (PAG) pathways that regulate normal cellular processes.

As demonstrated hereinbelow, a short-term effect of a primary stimulus on a target cell is to elevate the levels of specific unsaturated subspecies of phosphatidic acid (PA) and the corresponding diacylglycerol (DAG) formed by the hydrolysis of this PA. It is known that DAG may be generated by other secondary mechanisms such as the hydrolysis of phosphatidyl inositol (PI) or phosphatidyl ethanolamine (PE). However, the nature of the acyl groups of the DAG derived from these various sources is not identical. In particular, DAG derived from PA hydrolysis has a high level of sn-2 unsaturation not containing arachidonate (C20:4). This notation refers to the number of carbon atoms in the acyl residue (20) and the number of $\pi$ bonds (4). Typical fatty acid residues found in these PA/DAG subsets include those of oleic (C18:1), linoleic (C18:2) and docosahexanenoic acid (C22:6).

Further explanation of the model of cell activation and its relation to the compounds of the invention as found by applicants is set forth hereinbelow.

There are a large number of contexts in which it is desirable to protect target cells from primary stimuli which are the result of, for example, disease states (such as malignancy, autoimmune diseases, or infection) or of medical intervention (such as bone marrow transplantation or chemotherapy) which have negative sequelae in the target cell. This protection can be achieved by the method of the invention.

Some compounds related to those useful in the method of the invention have been suggested for medical use in other contexts. Pentoxifylline (1-(5-oxohexyl)-3,7-dimethylxanthine), abbreviated PTX herein, is one member of this class of xanthine derivatives which has seen widespread medical use for the increase of blood flow. PTX and its use as a vasodilator are disclosed in U.S. Pat. Nos. 3,422,307 and 3,737,433. The nature of the metabolism of PTX was summarized by Davis, P. J. et al., *Applied Environment Microbiol* (1984) 48:327-331. Some of the metabolites are also among the compounds of the invention. The immediate reduction product which is the primary metabolite of PTX—1-(5-hydroxyhexyl)-3,7dimethyxanthine, also designated M1—was disclosed to increase cerebral blood flow in U.S. Pat. Nos. 4,515,795 and 4,576,947.

In addition, a number of patents have issued on the use of tertiary alcohol analogs to compounds of this class in enhancing cerebral blood flow. These include U.S. Pat. Nos. 4,833,146 and 5,039,666.

Furthermore, U.S. Pat. No. 4,636,507 describes the ability of PTX and its primary metabolite, M1, to inhibit chemotaxis in polymorphonuclear leukocytes that normally respond to a known stimulator of chemotaxis. The ability of PTX and related tertiary alcohol substituted xanthines to inhibit the activity of certain cytokines on chemotaxis is disclosed in U.S. Pat. No. 4,965,271 and U.S. Pat. No. 5,096,906. Administration of PTX and GM-CSF decrease tumor necrosis factor (TNF) levels in patients undergoing allogeneic bone marrow transplant (Bianco, J. A. et al., *Blood* (1990) 76: Supplement 1 (522A)). The reduction in assayable levels of TNF was accompanied by a significant reduction in transplant-related complications. However, in normal volunteers, TNF levels are higher among PTX recipients. It does not, therefore, appear that elevated levels of TNF per se are the primary cause of such complications.

It has now been found that the compounds described hereinbelow can be used systematically to maintain the homeostasis of a large number of target cells in response to a variety of stimuli. In addition, compositions suitable for administration and routes to administer such compounds which permit effective dosages to be provided are disclosed.

Disclosure of the Invention

The invention is directed to the use of substituted xanthines containing at least one epoxide derivatized side chain in modulating cellular response to external or in situ primary stimuli, as well as to specific modes of administration of such compounds in effective amounts.

Thus, in one aspect, the invention is directed to a method to modulate the response of a target cell to a stimulus, which method comprises contacting said cell with an effective amount of a compound of the formula,

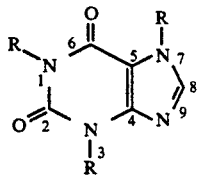

(1)

including the resolved enantiomers and/or diastereomers and mixtures thereof wherein each of one or two R is independently

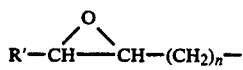

(2)

wherein n is 1-16 and R' is H or alkyl(1-4C); and wherein each remaining R is independently H, alkyl(1-6C), alkenyl(1-6C) or benzyl; and wherein said alkyl or alkenyl may be substituted by a hydroxyl, halo, or di-methylamino group, and/or interrupted by an oxygen atom.

In other aspects, the invention is directed to compounds of formula 1 per se, and to pharmaceutical compositions containing them.

When a cell is stimulated, elevated levels of a subset of phosphatidic acid (PA) containing sn-2 non-arachidonate unsaturation and diacylglycerol (DAG) derived from this PA are caused to form in the short term by the stimulating agent. Compounds of the invention effect a diminution in these elevated levels, and the diminution is equal to or greater than the diminution effected by treating the cells with pentoxifylline (PTX) at a concentration of 0.5 mM. The result is to modulate the response of the target cell to the stimulus. As further explained hereinbelow, this effect, analogous to that of PTX, results from blockage of a specific activation pathway that does not involve phosphatidyl inositol (PI) but rather derives from phosphatidic acid (PA) that is largely composed of 1,2-diunsaturated and 1-alkyl, 2-unsaturated species. The compounds of the invention, like PTX, are shown to inhibit the enzymes involved in this pathway.

In other aspects, the invention is directed to methods to decrease proliferation of tumor cells in response to an activated oncogene; to stimulate hematopoiesis in the presence of agents which inhibit hematopoiesis, such as chemotherapeutic agents; to methods to suppress the activation of T-cells in the presence of antigen and the secretion of antibodies by B-cells in the presence of antigen; to suppress the activation of macrophage by endotoxins or GM-CSF; to enhance the resistance of mesenchymal cells to tumor necrosis factor (TNF); to inhibit the proliferation of smooth muscle cells in response to growth factors; to inhibit the activation of T-cells and viral replication in response to human immunodeficiency virus; to inhibit the proliferation of kidney mesangial cells in response to IL-1; to prevent suppression of Steel factor, G-CSF, oncostatin M or IL-6 in bone marrow stromal cells in response to TNF, prevent production of macrophage inflammatory protein-1α (mip1α) by macrophage or monocytes or of platelet factor-4 by megakaryocytes, fibroblasts or macrophage in response to TNF, endotoxin or IL-1, suppress expression of adhesion molecules in endothelial cells, suppress proliferation of kidney mesangial cells in response to IL-1, mip1α, PDGF or FGF, prevent toxicity in kidney glomerular or tubular cells in response to cyclosporin A or amphotericin B, prevent cytotoxic effects in gastrointestinal or pulmonary epithelial cells in response to a cytotoxic drug or radiation, to enhance the antitumor effects in tumor cells in response to a nonalkylating antitumor agent, to suppress the production of metalloproteases in a glomerular epithelial cell in response to IL-1, to inhibit production of osteoclast-activating factor (OAP) by osteoclasts in response to IL-1, to inhibit degranulation of mast cells and basophils in response to IgE, to modulate signal transduction of the neurotransmitters epinephrine and acetylcholine in neural pathways utilizing these transmitters, and the like.

The cells to be affected may either be contacted with the compound of the invention in vitro culture, in an extracorporeal treatment, or by administering the compound of the invention or mixtures thereof to a subject whose cells are to be affected.

In still another aspect, the invention is directed to a method to administer the compounds of the invention to a mammalian subject comprising coadministering an effective amount of an agent which reduces the activity of the enzyme P450. In particular, coadministration of certain compounds of the invention along with a quinolone enhances their effect.

Modes of Carrying Out the Invention

Figure 1:
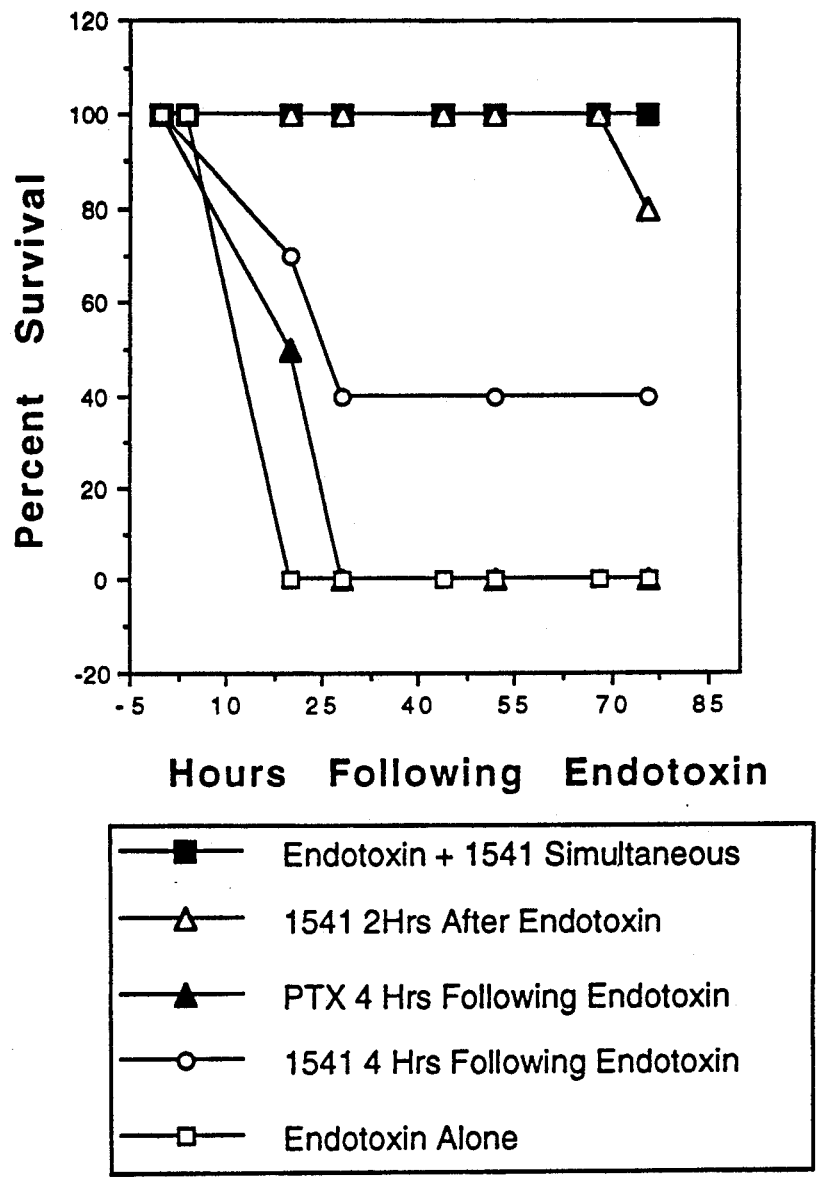
FIG. 1 shows the effect of the invention compound CT-1541 on protecting mice from lethal endotoxin challenge.

The invention is directed to methods of controlling cellular behavior which take advantage of the effect of certain xanthine derivatives on a particular phase of the secondary messenger pathway system. In particular, this aspect of the pathway is summarized in the following diagram, which uses the following abbreviations:

PE=phosphatidyl ethanolamine
LPE=lysophosphoethanolamine
PA=phosphatidic acid
LPA=lysophosphatidic acid
DAG=diacylglycerol
LPLD=lysophospholipase-D
LPAAT=lysophosphatidic acid acyl transferase
PAPH=phosphatidic acid phosphohydrolase
PLA2=phospholipase A-2.
PLD=phospholipase D
PAA=phosphoarachidonic acid
PLA-2=phospholipase A2
PC=phosphatidyl choline "remodeled" PA, cyclic pathway=PAA, LPA, PA and DAG intermediates substituted with L-saturated, 2-linoleoyl- or 1,2-dileolyl/1,2-sn-dilinoleoyl at the indicated sn1 and sn2 positions.

"Classical PI Pathway"=PI, DAG, PA intermediates substituted with 1-stearoyl, 2-arachidonoyl fatty acyl side chains.

"PLD-generated PA"=PE, PC, LPA, PA and DAG intermediates substituted with, e.g., 1,2-sn-dioleoyl-, 1-alkyl, 2-linoleoyl-, and 1-alkyl, 2-docosahexaneoyl-side chains.

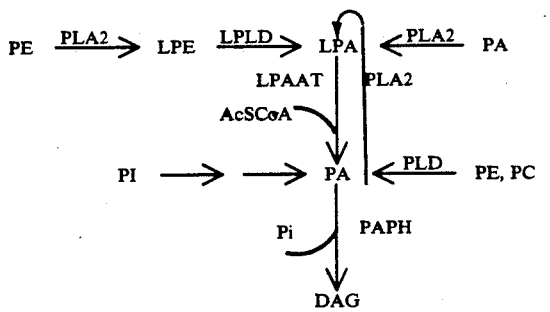

As shown in the above diagram, lysophosphatidic acid transferase (LPAAT) effects the synthesis of phosphatidic acid (PA) from lysophosphatidic acid (LPA) by incorporation of an acyl group from acyl CoA. Hydrolysis of the phosphate moiety by PA phosphohydrolase (PAPH) results in the formation of DAG. These aspects of the pathway appear to be activated immediately (within a minute) upon stimulation by a primary stimulus acting at the receptor on the cellular surface. The immediate detectable effect, as shown hereinbelow, is an elevation of levels of PA and DAG. Administration of the compounds of the invention reverse this elevation.

The inventors herein have shown that each membrane phospholipid subclass such as PA, PI, PE, phosphatidyl choline (PC) and phosphatidyl serine (PS) reaches a stable content of characteristic fatty acyl side chains due to cyclic remodeling of the plasma membrane as well as turnover for each subclass. PA is quite stable and present in small quantities. PA in resting cells is largely saturated, containing a significant amount of myristate, stearate and palmitate. In representative resting cells, PC consists mostly of acyl palmitate in the sn-1 position and oleate in the sn-2 position. PE and PI are predominantly composed of sn-1 stearate and sn-2 arachidonate. Due to this characteristic content of acyl groups in the sn-1 and sn-2 positions, the origin of any PA species may be deduced from the nature of the acyl groups—e.g., if PA is derived from PC through the action of PLD, it will contain the characteristic acyl side chains of PC substrate processed through this pathway. Further, due to this characteristic sn-1 and sn-2 acyl content, the origin of any 1,2,sn-substrate species may be differentiated as to its origin. This is qualified by the necessity of knowing whether or not the phospholipid species passes through a PA form previous to hydrolysis to DAG. As shown above, the lyso-PA that is converted to PA and thence to DAG may be shown. The complexities of these pathways can be sorted by suitable analysis of the fatty acyl side chain types of intermediate in cells at various times after stimulation.

It has been demonstrated by the inventors herein that in certain mesenchymal cells, such as rat/human cells, several secondary signaling pathways may be activated in tandem, simultaneously or both. For example, PDGF stimulates the formation of PA through the action of PLD, followed in time by formation of DAG through the action of PAPH; concurrently, another species of DAG is generated from PI through the classical phosphoinositide pathway. In many of the cells examined, DAG is derived from both PA that is being remodeled through a cycle whereby PAA is sn-2 hydrolyzed by PLA-2, followed by sn-2 transacylation by LPAAT, and a PLD-pathway from PA that is generated from either PI or PC substrates by PLD.

As the methods developed by the inventors herein have permitted the differentiation of the various subspecies of, for example, PA and DAG, it has been found that several subspecies are sometimes formed simultaneously. For example, in rat glomerular epithelial cells after stimulation with IL-1, three different DAG species are formed, one derived from PA remodeled by the remodeling mechanism described above involving LPAAT, one derived from PA derived from PLD, and one derived from PI. The "remodeled" PA is characterized as 1-saturated, 2-linoleoyl PA, and 1,2-dioleolyl/1,2-sn-dilinoleoyl PA. The DAG derived from these Pas has the latter fatty acyl side-chain composition as confirmed by mass spectrometry. The DAG derived from PI is largely 1-stearoyl, 2-arachidonoyl and separates from the PA-derived DAG.

The compounds of the invention, include inhibitors of subspecies of LPAAT in PAPH enzymes with substrate specificity for intermediates with 1,2-diunsaturated and 1-alkyl,2-unsaturated subspecies. One representative example of such an inhibitor is the parent oxo compound, PTX, that blocks PAPH in a specific activation pathway that does not involve PI but rather derives from PA that is largely composed of 1,2-diunsaturated and 1-alkyl,2-unsaturated subspecies. This was shown, for example, by the demonstration that human mesangial cells stimulated with TNF produce DAG from PI and regenerate PI in the absence and the presence of PTX. In the latter system there is no evidence to suggest that PA or DAG are derived from sources other than PI. The HPLC tracing and mass spectrometry techniques of the present invention permit subtle, complex evaluation of the formation of PI and DAG subspecies which are uniform and relatively monotonous, i.e., one type of signaling molecule not several, consonant with a consistent, non-radiating type of signal.

It should be emphasized that the compounds of the invention affect that subset of PAPH and LPAAT that relates to substrates with unsaturated fatty acids other than arachidonate in the sn2 position, not the housekeeping forms of these enzymes that serve the PI pathway. Furthermore, this subset like many enzymes, is composed of isoenzymes. Each of the invention compounds will have a particular spectrum of activity with respect to the isozyme members of the PAPH and LPAAT subset families.

It was thus shown that different concentrations of PTX specifically blocks formation of remodeled PA through the PA/DAG pathway; namely, 1) at high PTX concentrations by blocking formation of PA subspecies at LPAAT; 2) at low PTX concentrations by blocking the formation of PA-derived DAG at PAPH. In the presence of PTX PA continues to form through the action of phospholipase D, and DAG is also formed through the action of phospholipase C on PC and PI. The latter pathways are not inhibited by the compounds of the invention or PTX. In PTX-treated cells, DAG derived from remodeled and PLD-generated PA is diminished, for example, 1,2-sn-dioleoyl DAG, 1-alkyl,2-linoleoyl DAG and 1-alkyl,2-docosahexaneoyl DAG.

In general, the specific relevant PA and corresponding DAG measured by an assay described below and affected by the compounds of the invention are referred to generally as having fatty acyl sidechain in the sn-1 and sn-2 positions that are unsaturated and non-arachidonate.

The ability of the assay system to detect these specific intermediates of PA and DAG permits discrimination of the relevant substrates and enzymes that constitute the novel pathway for alternative phospholipid metabolism that is a subject of the invention.

Assays for developing new therapeutic agents, based upon the present disclosure, are set forth in detail below. Briefly, since the metabolic enzymes involved in the subject alternative phospholipid metabolic pathway exhibit exquisite specificity for different acyl sidechains and isomeric forms of substrates, drugs with improved therapeutic efficacy and potency can be provided by using the compounds of the invention.

In Vitro Assay for the Effects of the Invention Compounds

The effect of the compounds of the invention can be demonstrated in vitro and in vivo. A simple assay involving incubation of target cells with primary stimulus in the presence or absence of the xanthine of the invention followed by extraction and analysis of lipid content is diagnostic of the levels of various members of the foregoing pathway as characterized by their fatty acyl content. This assay indirectly measures the effect of the xanthine derivative on the relevant enzymes lysophosphatidic acid acyltransferase (LPAAT) and phosphatidic acid phosphoryl hydrolase (PAPH). In general, inhibition of these enzymes is effected by the xanthine of the invention, thus resulting in lowering of the levels of the relevant species of the particular acylated subspecies of PA and DAG intermediates.

The compounds of the invention are shown to modulate the effects of primary stimuli which elevate levels of the relevant subspecies of PA and DAG using the assay system of the invention. In general for the assay, the cells to be tested are first incubated with the primary stimulating agent for various time periods and fixed in ice-cold methanol.

To test the effect of the compound of the invention, the candidate compound is included in the initial incubation at various concentrations.

The lipids are extracted using, for example, chloroform:methanol 2:1 (v/v), and the extracts are then subjected to HPLC as described by Bursten and Harris, *Biochemistry* (1991) 30:6195-6203. In this method, a Rainin mu-Porasil column is used with a 3:4 hexane:propanol organic carrier and a 1-10% water gradient during the first 10 minutes of separation. Detection of the peaks in the elution pattern is by absorption in the range of ultraviolet which detects isolated double bonds. Thus, the relevant peaks of unsaturated PA and DAG are shown in the elution pattern. It is important to note that the assay method permits discrimination between various forms of PA and DAG so that those relevant to the pathway affected by the (R) or (S) compounds of the invention can be measured directly. Confirmation of the nature of the acyl substituents of these components is accomplished using fast-atom bombardment mass spectroscopy. Thus, the relevant unsaturated (non-arachidonic) PA and DAG subspecies may be detected. The time periods employed are 5-60 seconds after stimulation with the primary stimulus, such as a cytokine. This technique permits assessment of the levels of various lipid components as a function of time.

Although the foregoing outline of the assay is presented with respect to use of suitable target cells, subcellular units also serve as suitable sources of enzyme activity for the assay. Included among such subcellular entities are microsomes derived from mesenchymal and/or ectodermal cells, particularly microsomes from marrow stromal cells or human or rat mesangial cells; microsomes or synaptosomes derived from bovine brain; plasma membrane-enriched microsomes or plasma membranes derived as described in Bursten et al., *J Biol Chem* (1991) 226:20732-20743, incorporated herein by reference; detergent-solubilized microsomes; synaptosomes, and membranes or other cell preparations solubilized using, for example, NP-40, Miranal, SDS or other neutral detergents; and detergent-solubilized or further purified preparations of cell proteins, including the proteins LPAAT and/or PAPH.

Compounds of the Invention

The xanthine derivatives of the invention contain at least one substituent which is an epoxy of an alkyl group. Thus, at least one substituent R is of the formula

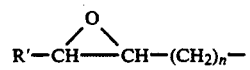

wherein n is 1-16 and R' is H or alkyl (1-4C). Preferred values of n are 3-12, particularly 5-9. R' is preferably H or methyl.

Those embodiments are preferred wherein a single alkyl epoxide substituent is at position 1 of this xanthine nucleus, or where alkyl epoxide substituents are at positions 1 and 7. Also preferred, are those compounds of the invention wherein a single R substituent which is an epoxy alkyl substituent is at position 7 of this xanthine nucleus.

The remaining R substituents are independently H, alkyl (1-6C), alkenyl (1-6C) or benzyl wherein the alkyl or alkenyl substituents may be further substituted with a hydroxy group, halo, dimethylamine and/or may be interrupted by an oxygen atom. Suitable embodiments for the remaining R groups include methyl, ethyl, isopropyl, n-propyl, isobutyl, n-butyl, t-butyl, 2-hydroxyethyl, 3-hydroxypropyl, 3-hydroxy-n-butyl, 2-methoxyethyl, 4-methoxy-n-butyl, 5-hydroxyhexyl, 2-bromopropyl, 3-dimethylaminobutyl, 4-chloropentyl and the like. Particularly preferred substituents are ethyl or methyl or H, and especially methyl or H. Particularly preferred compounds of the invention are also exemplified hereinbelow.

The compounds of the invention may be provided as enantiomeric or diastereomeric mixtures or in resolved or partially resolved forms. Standard procedures are used for resolution of optical isomers.

It is contemplated that the different enantiomeric variants (e.g., stereoisomers and chiral forms) of the xanthines will have different drug activities, based upon their differential ability to inhibit PAPH and LPAAT. The compounds of the invention have at least one asymmetric carbon atom and thus present different (R) and (S) stereoisomers; many of the compounds of the invention have two chiral centers and thus have four optical isomers.

By an optical isomer substantially free of the corresponding enantiomer and/or diastereomers is meant at least about 85% relevant optical isomer, preferably at least about 95% relevant optical isomer and especially at least about 99% or higher relevant optical isomer, but most preferably where the amount of other optical forms is undetectable.

In addition the activity of individual compounds of the invention including the chiral forms may vary among the isozyme members of the LPAAT and PAPH subsets to which the invention compounds are directed.

Any OH groups present in the compounds of the invention can be esterified by conventional methods such as reaction with the acyl halides or anhydrides of pharmaceutically acceptable acids, including alkanoic acids, amino acids, aromatic acids and the like, such as acetic acid, pivalic acid, benzoic acid and the like. Furthermore, dimethylamino-substituted forms may be prepared as the acid addition salts.

The compounds of the invention which are in the form of pharmaceutically acceptable esters can be prepared by conventional procedures for esterifying alcohols, such as direct reaction with the desired acid, acid halide, acid salt or acid anhydride usually at ambient temperature and optionally in the presence of an inert solvent.

The compounds of the invention are generally prepared by methods understood in the art. Alkylene groups which can subsequently be oxidized to the epoxides are substituted on the desired position of the xanthine nucleus by reaction of the suitably substituted xanthine with the ω-bromoalkene in the presence of a strong base and in a polar aprotic solvent. For example, for those embodiments wherein the R at positions 3 and 7 are both alkyl and the R at position 1 is the epoxyalkyl, the appropriate 3,7-dialkylxanthine is treated with the ω-bromo-1-alkene in the presence of strong base and the resulting 1-(ω-alkenyl)-3,7-dialkylxanthine is recovered and oxidized with a suitable peroxide such as a peroxybenzoic acid. This oxidation is conducted in an inert solvent and the product epoxide recovered using standard procedures.

The optical isomers of vincial diols can be obtained directly by oxidation of the ω-alkenyl-substituted xanthine in the procedure of Sharpless et al., *J Org Chem* (1992) 57:2768. These diols can then be cyclized to the optically active epoxide by the method of Szeja (*Synthesis* 1985 p. 983).

For compounds of the invention wherein the non-epoxy sidechain contains a hydroxyl group, suitable protection for the hydroxy group must be supplied prior to the alkylation of the xanthine nucleus. Suitable protecting groups include trimethylsilyl.

Illustrative compounds of the invention include:
1. 1-(5,6-oxidohexyl)-3,7-dimethylxanthine
2. 1-(7,8-oxidooctyl)-3,7-dimethylxanthine
3. 1-(2,3-oxidopropyl)-3,7-dimethylxanthine
4. 1-(4,5-oxidohexyl)-3,7-dimethylxanthine
5. 1-(17,18-oxidooctdecyl)-3,7-dimethylxanthine
6. 1-(15,16-oxidooctadecyl)-3,7-dimethylxanthine
7. 1-(14,15-oxidopentadecyl)-3,7-dimethylxanthine
8. 1-(11,12-oxidopentadecyl)-3,7-dimethylxanthine
9. 1-(9,10-oxidodecyl)-3,7-dimethylxanthine
10. 1-(6,7-oxidodecyl)-3,7-dimethylxanthine
11. 7-(5,6-oxidohexyl)-1,3-dimethylxanthine
12. 7-(7,8-oxidooctyl)-1,3-dimethylxanthine
13. 7-(2,3-oxidopropyl)-1,3-dimethylxanthine
14. 7-(4,5-oxidohexyl)-1,3-dimethylxanthine
15. 7-(17,18-oxidooctadecyl)-1,3-dimethylxanthine
16. 7-(15,16-oxidooctadecyl)-1,3-dimethylxanthine
17. 7-(14,15-oxidopentadecyl)-1,3-dimethylxanthine
18. 7-(11,12-oxidopentadecyl)-1,3-dimethylxanthine
19. 7-(9,10-oxidodecyl)-1,3-dimethylxanthine
20. 7-(6,7-oxidodecyl)-1,3-dimethylxanthine
21. 1-(5,6-oxidohexyl)-3-methyl-7-ethylxanthine
22. 1-(7,8-oxidooctyl)-3-(2-bromoethyl)xanthine
23. 1-(2,3-oxidopropyl)-3-(2-dimethylaminohexyl)xanthine
24. 1-(4,5-oxidohexyl)-3-(2-dimethylaminohexyl)-7ethylxanthine
25. 1-(17,18-oxidooctadecyl)-3-(3-hydroxypentyl)-7-(2bromoethyl)xanthine
26. 1-(15,16-oxidooctadecyl)-3-ethylxanthine
27. 1-(14,15-oxidopentadecyl)-3-methyl-7-(2-dimethylaminohexyl)xanthine
28. 1-(11,12-oxidopentadecyl)-3-benzyl-7-methylxanthine
29. 1-(9,10-oxidodecyl)-3,7-diethylxanthine
30. 1-(6,7-oxidodecyl)-3,7-(2-hydroxyethyl)xanthine
31. 7-(5,6-oxidohexyl)-1-methyl-3-ethylxanthine
32. 7-(7,8-oxidooctyl)-1-(2-bromoethyl)xanthine
33. 7-(2,3-oxidopropyl)-1-(2-dimethylaminohexyl)xanthine
34. 7-(4,5-oxidohexyl)-1-(2-dimethylaminohexyl)-3-ethylxanthine
35. 7-(17,18-oxidooctadecyl)-1-(3-hydroxypentyl)-3-(2-bromoethyl)xanthine
36. 7-(15,16-oxidooctadecyl)-1-ethylxanthine
37. 7-(14,15-oxidopentadecyl)-1-methyl-3-(2dimethylaminohexyl)xanthine
38. 7-(11,12-oxidopentadecyl)-1-benzyl-3-methylxanthine
39. 7-(9,10-oxidodecyl)-1,3-diethylxanthine
40. 7-(6,7-oxidodecyl)-1,3-(2-hydroxyethyl)xanthine
41. 1,7-di(1-(5,6-oxidohexyl)-3-methylxanthine
42. 1,7-di(1-(7,8-oxidooctyl)-3-methylxanthine
43. 1,7-di(1-(2,3-oxidopropyl)-3-methylxanthine
44. 1,7-di(1-(4,5-oxidohexyl)-3-methylxanthine
45. 1,7-di(1-(17,18-oxidooctdecyl)-3-methylxanthine
46. 1,7-di(1-(15,16-oxidooctdecyl)-3-methylxanthine
47. 1,7-di(1-(14,15-Oxidopentadecyl)-3-methylxanthine
48. 1,7-di(1-(11,12-oxidopentadecyl)-3-methylxanthine
49. 1,7-di(1-(9,10-oxidodecyl)-3-methylxanthine
50. 1,7-di(6,7-oxidodecyl)-3-methylxanthine
51. 1,7-di(1-(5,6-oxidohexyl)-3-propyl-1-xanthine
52. 1,7-di(1-(7,8-oxidooctyl)-3-(2-bromoethyl)xanthine
53. 1,7-di(1-(2,3-oxidopropyl)-3-(2-dimethylamino)xanthine
54. 1,7-di(1-(4,5-oxidohexyl)-3-(2-dimethylaminopentyl) xanthine
55. 1,7-di(1-(17,18-oxidooctadecyl)-3-(3-hydroxypentyl) xanthine
56. 1,7-di(1-(15,16-oxidooctadecyl)-3-ethylxanthine
57. 1,7-di(1l-(14,15-oxidopentadecyl)-3-(4-chloropentyl) xanthine
58. 1,7-di(1-(11,12-oxidopentadecyl)-3-benzylxanthine
59. 1,7-di(1-(9,10-oxidodecyl)-3-(2-oxidoethyl)xanthine
60. 1,7-di(6,7-oxidodecyl)-3-(2-hydroxyethyl)xanthine
either as racemates or as resolved optical isomers.

Uses of the Invention Compounds and Pharmaceutical Formulations

The compounds of the invention provide a mechanism to maintain homeostasis in cells contacted by primary stimuli through mitigating the effects of these primary stimuli on the secondary signaling pathways invoked within seconds of the primary stimulus.

The stimuli referred to herein are of wide variety and include, for example a variety of cytokines, growth factors, oncogene products, putatively therapeutic agents, irradiation, viral infection, toxins, bacterial infection and the products thereof, and the like. Any stimulus which, if not counteracted, has a deleterious effect on the target cell is included within the definition.

For example, the compounds of the invention are used in connection with patients undergoing bone marrow transplantation (BMT), regardless of whether the BMT is matched allogeneic, mismatched allogeneic, or autologous. Patients receiving autologous transplants are aided by treatment with compounds of the invention even though they do not necessarily need to be administered immunosuppressive agents, since they do not develop graft-versus-host disease (GVHD). However, the toxic effect of the chemotherapy or radiation therapy used in connection with the disease, in response to which the transplantation has been performed, constitutes a negative stimulus with regard to the patients' cells.

In general, all patients undergoing BMT require doses of chemotherapy, with or without total body irradiation, that exceed the lethal dose for normal bone marrow recovery. This provides the rationale for using either stored patient marrow or donor marrow to rescue the patient.

In general, chemotherapy and radiation are delivered to the patient for 7–10 consecutive days before the new or stored bone marrow is infused. The day on which the marrow is given to the patient is referred to as day 0 of the transplant; previous days on which the patient received chemo/radiation are designated by negative numbers. Subsequent days are referred to by positive numerals.

The median time in which negative responses in BMT recipients occurs is within the first 100 days after transplant. Therefore, statistically, if patients survive through day 100, their chances for continued survival are significantly enhanced. As shown in the examples hereinbelow, compounds of Formula I are able to increase the percentage of patients who survive. The percentage of fatalities within the first 100 days considered acceptable is 15–20% for "good risk" patients and 30–40% for "high risk". These fatalities are due to the direct effects of high doses of chemo/radiation; in addition, GVHD contributes to the death rate in allogeneic marrow recipients.

Other indications for which it is useful to administer the compounds of the invention include the presence of a tumor burden, a hormone-related disorder, a neurological disorder, an autoimmune disease, inflammation, restenosis, hypertension, unwanted immune response, viral infection, nephritis, mucositis, and various allergic responses. Prevention of allergic responses include prevention of acute allergic response and thus moderation or prevention of rhinorrhea, serious drainage, diffuse tissue edema, and generalized pruritus. Other symptoms of chronic allergic response include, as well as the foregoing, dizziness, diarrhea, tissue hyperemia, and lacrimal swelling with localized lymphocyte infiltration. Allergic reactions are also associated with leukotriene release and the distal effects thereof, including asthmatic symptoms including development of airway obstruction, a decrease in FEV1, changes in vital capacity, and extensive mucus production.

Other suitable subjects for the administration of compounds of the invention, include patients being administered toxic agents for the treatment of tumors, such as chemotherapeutic agents or irradiation therapy, as well as treatment with biological response modifiers such as IL-2 and tumor suppressing cells such as lymphokine activated killer cells (LAK) and tumor-infiltrating lymphocytes (TIL cells); patients suffering from neoplasias generally, whether or not otherwise treated including acute and chronic myelogenous leukemia, hairy cell leukemia, lymphomas, megakaryocytic leukemia, and the like; disease states caused by bacterial, fungal, protozoal, or viral infection; patients exhibiting unwanted smooth muscle cell proliferation in the form of, for example, restenosis, such as patients undergoing cardiac surgery; patients who are afflicted with autoimmune diseases, thus requiring deactivation of T and B cells, and patients who have neurological disorders.

The compounds of the invention further are able to decrease the enhanced levels of the relevant PA and DAG resulting from stimulation of synaptosomes with acetylcholine and/or epinephrine. This suggests that the effects of the compounds of the invention are to both enhance the release of inhibitory neural transmitters such as dopamine, and to modulate the distal "slow current" effects of such neurotransmitters.

Thus, the drugs of the invention are also useful to raise the seizure threshold, to stabilize synapses against neurotoxins such as strichnine, to potentiate the effect of anti-Parkinson drugs such as L-dopa, to potentiate the effects of soporific compounds, to relieve motion disorders resulting from administration of tranquilizers, and to diminish or prevent neuron overfiring associated with progressive neural death following cerebral vascular events such as stroke. In addition, the compounds of the invention are useful in the treatment of norepinephrine-deficient depression and depressions associated with the release of endogenous glucocorticoids, to prevent the toxicity to the central nervous system of dexamethasone or methylprednisolone, and to treat chronic pain without addiction to the drug. Further, the compounds of the invention are useful in the treatment of children with learning and attention deficits and generally improve memory in subjects with organic deficits, including Alzheimer's patients.

While dosage values will vary, good results are achieved when the xanthines of the invention are administered to a subject requiring such treatment as an effective oral, parenteral, or intravenous sublethal dose of about 200 mg to about 7500 mg per day. A particularly preferred regimen for use in leukemia is 4–50 mg/kg body weight. It is to be understood, however, that for any particular subject, specific dosage regimens should be adjusted to the individual's need and to the professional judgment of the person administering or supervising the administration of the xanthines; the dosages set forth herein are exemplary only and do not limit the scope or practice of the invention.

Coadministration With a Quinolone

The coadministration in vivo of the compounds of the invention along with an inhibitor of P450 results in an enhanced effect. It is believed that this effect in vivo is due to the inhibition of the degradation pathway for the compounds of the invention; in particular with respect to the dealkylation at the N7 position. While the basis for this effect may not be the same in vitro, an in vitro assay described below is useful in assessing candidate drugs for coadministration with the xanthine compounds of the invention, as well as for evaluating the desirability of quinolone coadministration for particular invention compounds. It thus is also demonstrable in vitro that a compound capable of inhibiting P450, such as a quinolone, enhances the effect of the xanthine of the invention, thus lowering the dosage levels required, or permitting strong synergistic effects at the same dosage. For example, a transformed cell line containing an activated oncogene is shown to be phenotypically modified by the compounds of the invention; coadministration thereof with ciprofloxacin can have a dramatically better effect than either alone.

Thus, the compounds of the invention, alone or in combination with a P450 inhibitor, are effective in vivo to modulate cellular behavior as described above. The compounds of the invention in combination with a quinolone can also reverse the negative effects of various agents used in "therapy." Transplantation patients who have undergone chemotherapy or radiation therapy and who have been administered prednisone and/or cyclosporin A as immunosuppressive agents benefit by coadministration of the compounds of the invention and the P450 inhibitor quinolone ciprofloxacin (CIPRO).

The desirability of coadministration of the xanthine of the invention with the P450 inhibitor varies with the choice of compound of the invention. For particularly active forms of the xanthine derivatives of the invention coadministration may not be necessary or helpful. For other invention compounds the coadministration of the quinoline may be desirable.

The desirability of coadministering an inhibitor of P450 in vivo can be determined using the above described assay method for activity of the invention compounds. This method, based on lipid extraction followed by HPLC, may also be employed to evaluate the effect of coadministration with quinoline. In such assays, the incubation with primary stimulus is conducted in the presence of the compound of the invention and in the presence or absence of the candidate P-450-inhibiting compound. The effect of the presence of the P-450 inhibiting compound is then used as a basis for judgment.

In an additional assay method, the effect of coadministering a xanthine compound of the invention with an inhibitor for P-450 can be assessed using transformed NIH3T3-D5C3 cells and comparing the effect on transformation phenotype among control, incubation with the xanthine of the invention alone, and coincubation of the xanthine of the invention with the P450 enzyme inhibitor.

Compounds that inhibit P-450, besides the ciprofloxacin illustrated hereinbelow, include other suitable agents (mg range daily dosage) as follows: propranolol (20-100), metaprolol (20-100); verapamil (100-400), diltiazem (100-400), nifedipine (60-100); cimetidine (400-2,400); ciprofloxacin (500-2000), enoxacin (500-2,000), norfloxacin (500-2000), ofloxacin (500-2,000), pefloxacin (500-2,000); erythromycin (100-1,000), troleandomycin (100-1,000); ketoconizole (100-2,000), thiabenzadole (100-1,000); isoniazid (100-1000); mexiletine (100-1,000); and dexamethasone (1-100 mg).

For combination therapy, the compounds of the invention and the P450 inhibitors can be administered individually or in a single composition. The suitable formulation will depend on the nature of the disorder to be treated, the nature of the medicament chosen, and the judgment of the attending physician. In general, these compounds are formulated either for injection or oral administration, although other modes of administration such as transmucosal or transdermal routes may be employed. Suitable formulations for these compounds can be found, for example, in *Remington's Pharmaceutical Sciences* (latest edition), Mack Publishing Company, Easton, Pa.

The amount of xanthine of the invention in such compositions is such that a suitable dosage will be obtained. Preferred compositions and preparations according to the present invention are prepared so that an oral dosage unit form contains between about 1.0 mg and about 2000 mg of active compound.

Depending on the xanthine compound of the invention selected, the level of dosage can be appreciably diminished by coadministration of a P450 inhibitor such as the quinolone illustrated below; alternatively, without diminishing the dosage, a strong synergistic effect may be obtained with such a quinolone. Many P450 inhibitors and xanthine compounds of the invention are compatible and can be formulated in a combined dosage. However, the compounds can also be coadministered separately.

Examples

The invention is illustrated by the following examples which should not be regarded as limiting the invention in any way. In these examples PTX means pentoxifylline.

Example 1

A. Synthesis of 1-(5,6-oxidohexyl)-3,7-dimethylxanthine

To a mixture of theobromine (5.53 g, 30.66 mmol) in 50 ml dimethylsulfoxide (DMSO) was added sodium hydride (883 mg, 36.79 mmoles) with vigorous stirring for 10 min after which a viscous slurry formed. To the mixture was added dropwise 6-bromo-1-hexene (5 g, 30.66 mmol) in 20 ml of DMSO. After stirring for 23 hr, the mixture was treated with water (100 ml) and extracted with ether (3×100 ml). The combined extracts were washed with water (2×50 ml), dried with magnesium sulfate and the solvent evaporated under vacuum to yield white crystals 7.7 g (29.39 mmol, 95.5% yield) of 1-(6-hexenyl)-3,7-dimethylxanthine.

To a stirred solution of 1-(6-hexenyl)-3,7-dimethylxanthine (2.5 g, 9.5 mmol) in 30 ml methylene chloride was added dropwise over 5 min a solution of 50-60% m-chloroperoxybenzoic acid (4.9 g, 14.3 mmol) in 20 ml methylene chloride. After stirring for 19 hr the mixture was treated with 20% aqueous sodium bisulfite solution (35 ml) and then extracted with methylene chloride (2×30 ml). The combined extracts were washed with saturated aqueous sodium bicarbonate solution (60 ml), dried over magnesium sulfate and the solvent evaporated under vacuum. Recrystallization of the residue from minimum methylene chloride/ether gave yellow crystals (1st batch=1.2 g, 4.32 mmol, 45.2% yield; 2nd batch from the mother liquor=0.260 g, 0.93 mmol, 9.8%) of 1-(5,6-oxidohexyl)-3,7-dimethylxanthine. The total yield was 55%.

B. Synthesis of 1-(7,8-oxidooctyl)-3,7-dimethylxanthine 1-(7,8-oxidooctyl)-3,7-dimethylxanthine was prepared by the same method as described with the exception that 8-bromo-1-octene was used as a starting material in place of 6-bromo-1-hexene. The resulting 1-7,8-oxidohexyl)-3,7-dimethylxanthine was epoxidized as described above for 1-(5,6-oxidohexyl)-3,7-dimethylxanthine.

Example 2

Synthesis of (S or R)-1-(5,6-oxidohexyl)-3,7-dimethylxanthine 1-(5-hexenyl)-3,7-dimethylxanthine, prepared as described above, was treated with the reagent "AD-mix alpha or AD-mix beta" according to the procedure described by Sharpless et al., J Oro Chem (1992) 57(10):2768, to yield (S or R)-1-(5,6 dihydroxyhexanyl)-3,7-dimethylxanthine, which was then converted to the R or S epoxide by treatment with tosylchloride-sodium hydroxide-benzyltriethylammonium chloride according to the method of Szeja (*Synthesis* (1985), p. 983).

Example 3

Synthesis of (S or R)-1-(2,3-oxidoprooyl)-3,7-dimethylxanthine

Theobromine was deprotonated with sodium hydride in DMSO as described above and then R or S epichlorohydrin in DMSO was added with stirring at 40° C. for 12 hours. The reaction mixture was worked up as described for the synthesis of 1-(5,6-oxidohexyl)-3,7-dimethylxanthine, to yield (S or R )-1-(2,3-oxidopropyl)-3,7-dimethylxanthine.

Example 4

Synthesis of (R or S)-1-(4,5-oxidohexyl)-3,7-dimethylxanthine

To a solution of 4-hexen-1-ol (1.22 g, 12.2 mmol) in methylene chloride (15 ml) was added mesyl chloride (1.54 g, 13.4 mmol). The mixture was cooled to 0° C. and triethylamine (1.85 g, 18.3 mol) was added dropwise. After 5 min, the mixture was warmed to room temperature and stirred for an additional 45 min. The mixture was treated with saturated sodium bicarbonate (25 ml) and the layers were separated with a funnel. The aqueous phase was extracted with methylene chloride (20 ml) and the combined organic extracts were dried over magnesium sulfate. The solvents were evaporated under vacuum to leave the desired mesylate, 4-hexen-1-methanesulfonate, as an oil. In typical fashion as described above, theobromine was deprotonated in DMSO and then alkylated with 4-hexen-1-methanesulfonate over 3.5 days. The mixture was treated with water (70 ml) and then extracted with ether (3×50 ml). The combined organic extracts were washed with water (50 ml) and dried over magnesium sulfate. The solvent was evaporated under vacuum to leave the desired 1-(4-hexenyl)-3,7-dimethylxanthine as a white solid (2.1 g, 67% yield). To a solution of the 1-(4-hexenyl)-3,7-dimethylxanthine (270 mg, 1.03 mmol) in methylene chloride (15 ml) was added saturated sodium bicarbonate (10 ml) followed by m-choroperoxybenzoic acid (50–60%, 889 mg, 2.58 mmol) over 1 min. The mixture was stirred for 20 hr, and then treated by careful addition of sodium metabisulfite (20%, 15 ml). The mixture was extracted with methylene chloride (3×15 ml). The combined organic extracts were washed with saturated sodium bicarbonate (3×20 ml), dried over magnesium sulfate and the solvent was evaporated under vacuum to leave the crude solid (150 mg). The material was purified by chromatography over silica gel (14 g) eluting with ethyl acetate (100 ml) followed by 8% methanol/chloroform (60 ml) to afford pure 1-(4,5-oxidohexyl)-3,7-dimethylxanthine (80 mg, 28% yield).

Example 5

Mixed Leukocyte Reaction

Peripheral blood mononuclear cells from two HLA-DR disparate individuals were isolated and cocultured for 6 days in a mixture of RPMI tissue culture medium and 20 percent human AB serum with and without test compounds. Test compounds, PTX; 1-(5,6-oxidohexyl)-3,7-dimethyl xanthine (CT-1541) and 1-(7,8-oxidooctyl)-3,7-dimethyl xanthine (CT-1553), in concentrations of 10-1000 $\mu$M are added at inception of the culture. Tritiated thymidine (1 $\mu$C/well) is added after 5 days of incubation and after 4 hours the cells are harvested in a cell harvester (Cambridge Technology Inc., Watertown, Mass.) and counted in a liquid scintillation counter. Activity is shown by the ability of the test compound to inhibit thymidine uptake.

Example 6

Assay for Protection From Lethal Endotoxin Challenge

Groups of 10 Balb/C mice were treated intravenously with 175 $\mu$g/mouse lipopolysaccaride (LPS) and injected intraperitoneally with CT-1541 (prepared as in Example IA) either simultaneously with the LPS or 2 or 4 hours following the LPS endotoxin challenge. Treatment was continued in each group with 100 mg/kg of CT-1541 three times per day for three days. PTX, used as a control, was injected 4 hours after LPS and treatment was continued at 100 mg/kg IP injection three times per day for three days as above. The results are shown in FIG. 1 as percent survival at various time points after endotoxin administration.

As shown in FIG. 1 when the mice were treated using endotoxin alone (open squares) the percent survival dropped to 0% at about 20 hours past injection. When treated with PTX 4 hours after administration of LPS (closed triangles) percent survival was 45% after 25 hours and 0% survival was reached only after 30 hours. When treated with CT-1541 4 hours following endotoxin administration (open circles) survival was 65% after 18 hours and 40% after 26 hours, a level of survival that was maintained during the 80 hour course of the experiment.

With administration of CT-1541 either simultaneously with LPS administration or 2 hours thereafter (closed squares and open triangles respectively) survival was maintained at 100% until 70 hours; after 70 hours survival in the group injected 2 hours after LPS administration dropped to 80%. Thus, CT-1541 is able to protect mice from endotoxin lethality.

Example 7

Assay for Inhibition of Adhesion

The ability of the compounds of the invention to inhibit the adhesion of human U937 cells to activated human umbilical vein endothelial cells (HUVEC) by the compounds of the invention is demonstrated by the following assay.

HUVEC cells (4000/well), seeded 72 hours in advance were activated with 50 ng/ml TNF-α for 12 hours. Various concentrations of either CT-1553 (Example 1B) or CT-1541 (Example 1A) were added to the HUVEC cultures 1 hour prior to addition of the TNFα. Comparable concentrations of PTX were used as a control. U-937 cells preloaded with fluorescent dye BCECF (BCECF= 2',7'-bis-(2-carboxyethyl)-5-(and-6)-carboxyfluorescein, acetoxymethyl ester), were added to each well (50,000/well) for 30 minutes and washed two times with PBS. Fluorescence was assayed on a fluorescent plate reader. The results were read as BCECF fluorescence in the presence of various concentrations of the test compounds. The amount of BCECF fluorescence therefore correlates to adhesion of U-937 cells to HUVEC.

Figure 2A:
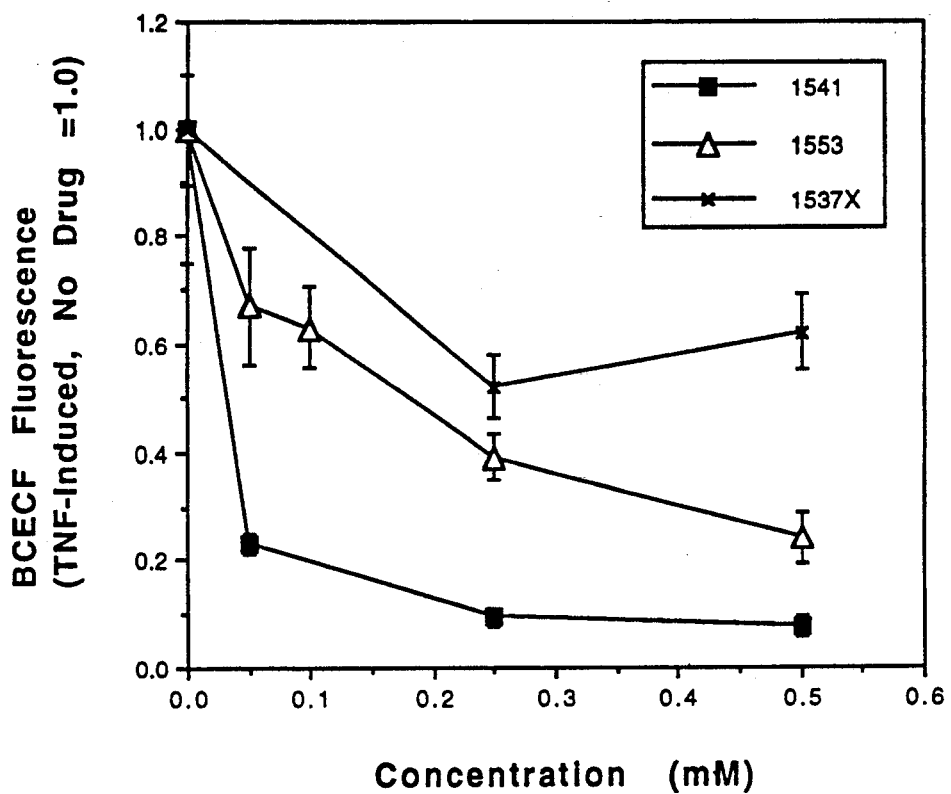
FIG. 2A is a graph showing the effect of inhibition of adhesion of U-937 cells to TNF activated human umbilical vein endothelial cells (HUVEC) by various compounds.

The results are shown in FIG. 2A plotting the concentration of the test compound in mM against BCEF fluorescence. The fluorescence of cultures to which TNF, but no drug, was added was set at 1.0. As shown in FIG. 2A, PTX (crosses) provided a 0.6 reading for fluorescence at 0.25 mM and a slightly higher fluorescence at 0.5 mM. On the other hand, CT-1541 (open triangles) provided 0.4 and 0.25 levels of fluorescence at 0.25 and 0.5 mM respectively; CT-1543 (closed squares) gave readings of 0.1 at both of these concentrations.

In a similar experiment, but substituting various concentrations of LPS in place of TNFα for the 12 hour activation, the effects of 0.25 mM CT-1541 added 1 hour prior to the addition of LPS was evaluated. The results of this assay are shown in FIG. 2B.

Figure 2B:
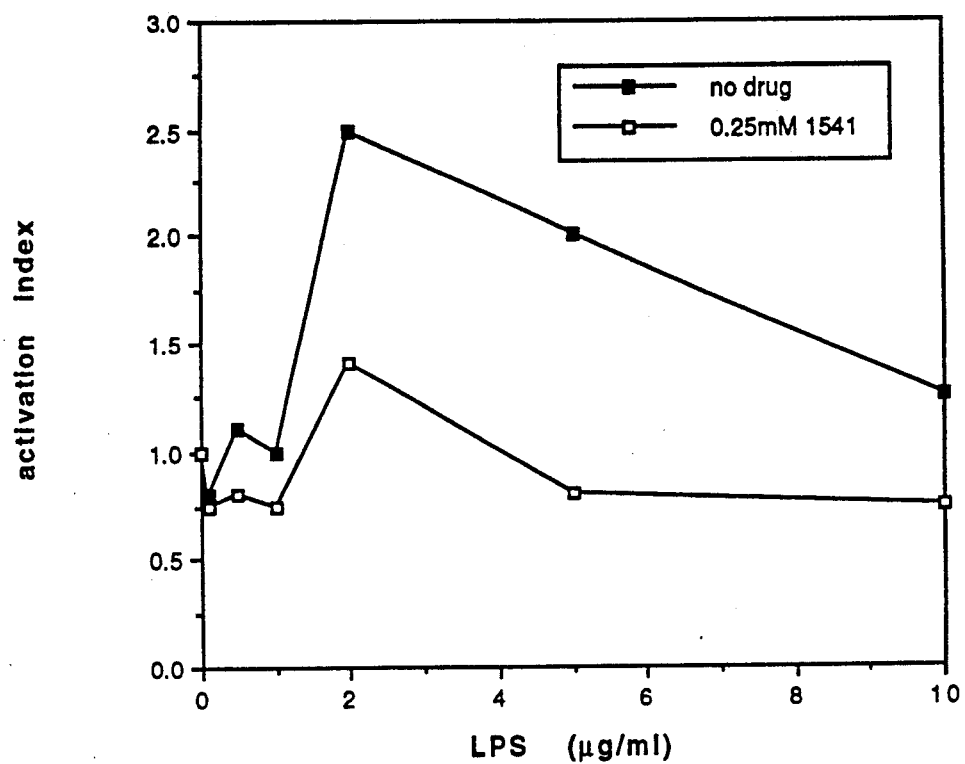
FIG. 2B shows the effect of lipopolysaccharide concentration on the activation of HUVEC in the presence and absence of invention compound.

FIG. 2B plots the LPS concentration in μg/ml against the activation index (activation index=number of adhering cells to activated endothelium/number of cells adhering to unactivated endothelium). As shown in FIG. 2B, when no drug is supplied (closed squares) maximal activation of 2.5 is found at 2 μg/ml LPS; lower levels of activation are obtained at lower and higher concentrations. When treated with 0.25 mM CT-1541 of Example 1A (open squares) 1 hour prior to addition of LPS a maximum activation index is also obtained at 2 mg/ml LPS but only at a level of 1.5.

Figure 2C:
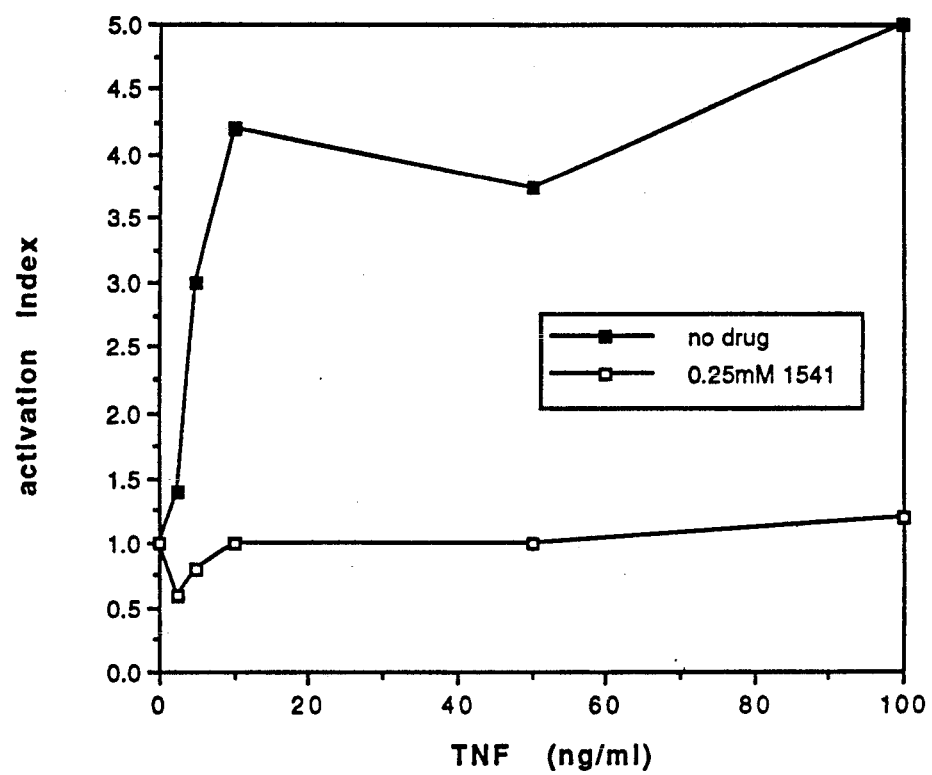
FIG. 2C shows the effect of TNF concentration on the activation of HUVEC in the presence and absence of invention compound.

In still another determination similar to that set forth for LPS, but using various concentrations of TNF for 12 hours as activating agent and using 0.25 mM CT-1541 as a test compound added 1 hour prior to addition of TNF, the results of FIG. 2C were obtained. FIG. 2C plots the concentration of TNF in ng/ml against activation index. In the absence of drug (closed squares), the activation index rises quickly from 1 to 4.2 in the presence of about 0 ng/ml TNF and is maintained at roughly this level within experimental error up to 100 ng/ml TNF. However, in the presence of 0.25 mM CT-1541, (open squares) no increased adhesion of U-937 cells is measured.

Example 8

Cytotoxicity to Tumor Cells

The cytotoxicity of CT-1541 (Example 1A) and CT-1553 (Example 1B) with respect to human breast cancer MCF-7 cells was tested in comparison to PTX.

MCF-7 cells ($10^4$/well on a 96 well microtiter plate) were treated with various concentrations of the test compounds. 48 hours later the cells were stained for viability using BCECF and fluorescence was analyzed using a Millipore fluorescent plate reader. Cells were stained with 10 ug/ml BCECF in full media for 30 min at 37° C. Only viable cells take up and cleave the non-fluorescent acetoxymethyl ester to the fluorescent carboxyfluorescein, which is retained in the cell and quantitated using a fluorescent plate reader (488 nm excitation with 525 nm emission).

Figure 3:
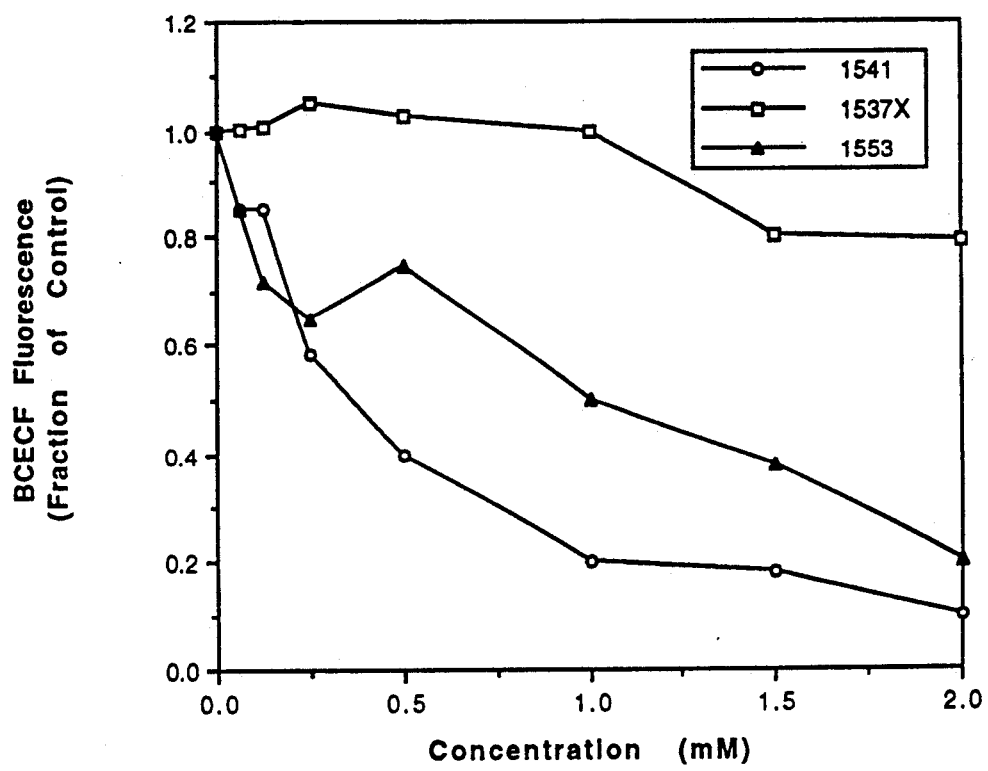
FIG. 3 shows the cytotoxicity of invention compounds to human breast cancer cell line MCF-7.

The results are shown in FIG. 3 which plots the concentration of the added drug in mM against BCECF fluorescence as a fraction of control. PTX (open squares) lowers BCECF fluorescence (i.e., decreases viability) only at a concentration of at least 1.5 mM, and then only slightly (0.85). CT-1553 (closed trangles) decreases flurorescence to 0.85 at about 0.01 mM and to about 0.7 at 0.1–0.5 mM. At 1 mM concentration, fluorescence is lowered to 0.5; at 2.0 mM flurorescence is roughly 0.2.

CT-1541 (open circles) shows a similar effect at low concentrations (less than 0.2 mM) and then is more cytotoxic. At 0.5 mM fluorescence is lowered to 0.4 and at 1.0 mM and above, fluorescence is approximately 0.2.

We claim:

1. A compound of the formula $$\underset{R}{\overset{R}{\underset{|}{N_1}}}\overset{O}{\overset{||}{\underset{6}{C}}}\overset{R}{\underset{5}{\overset{|}{N_7}}}_{8}$$
$$O=\overset{}{\underset{2}{C}}\quad\underset{\underset{R}{|}{N_3}}{}\overset{}{\underset{4}{C}}\overset{}{N_9}$$

(1)

including the resolved enantiomers and/or diastereomers and mixtures thereof wherein each of one or two R is $$R'-\overset{O}{\overset{/\,\backslash}{CH-CH}}-(CH_2)_n-$$

(2)

wherein n is 4-16 and R' is H or alkyl(1-4C); and wherein each remaining R is independently H, alkyl(1-6C), alkenyl(1-6C) or benzyl; and wherein said alkyl or alkenyl may be substituted by a hydroxyl, halo, or dimethylamino group, and/or interrupted by an oxygen atom.

2. The compound of claim 1 wherein the R at position 1 and/or position 7 is of the formula (2), and the remaining R are as above defined.

3. The compound of claim 1 wherein n is 3-12.

4. The compound of claim 1 wherein n is 5-9.

5. The compound of claim 1 wherein R' is methyl.

6. The compound of claim 1 wherein the R other than R of formula (2) are methyl or H.

7. The compound of claim 1 which is 1-(5,6-oxidohexyl)-3,7-dimethyl xanthine including the resolved optical isomers thereof.

8. The compound of claim 1 which is 1-(7,8-oxidooctyl)-3,7-dimethyl xanthine including the resolved optical isomers thereof.

9. The compound of claim 1 which is 1-(2,3-oxidopropyl)-3,7-dimethyl xanthine including the resolved optical isomers thereof.

10. A pharmaceutical composition comprising the compound of claim 1 in admixture with at least one pharmaceutically acceptable excipient.

11. A pharmaceutical composition which comprises an effective amount of the compound of claim 1 and an effective amount of an anti-P450 agent, in admixture with a pharmaceutically acceptable excipient.

12. The composition of claim 11 wherein said anti-P450 agent is a quinolone.

* * * * *